(12) United States Patent  
Fehling

(10) Patent No.: US 9,233,387 B2
(45) Date of Patent: Jan. 12, 2016

(54) FUNCTIONAL HEAD FOR A FRAGRANCE CONTAINER

(71) Applicant: Leopold Kostal GmbH & Co. KG, Luedenscheid (DE)

(72) Inventor: Andre Fehling, Dortmund (DE)

(73) Assignee: Leopold Kostal GmbH & Co. KG, Luedenscheid (DE)

( * ) Notice: Subject to any disclaimer, the term of this patent is extended or adjusted under 35 U.S.C. 154(b) by 201 days.

(21) Appl. No.: 13/922,357

(22) Filed: Jun. 20, 2013

(65) Prior Publication Data

US 2013/0277456 A1 Oct. 24, 2013

Related U.S. Application Data

(63) Continuation-in-part of application No. PCT/EP2012/051698, filed on Feb. 1, 2012.

(30) Foreign Application Priority Data

Feb. 4, 2011 (DE) .......................... 10 2011 010 277

(51) Int. Cl.
*A62C 13/62* (2006.01)
*B05B 17/00* (2006.01)
*A61L 9/12* (2006.01)
*B60H 3/00* (2006.01)

(52) U.S. Cl.
CPC .. *B05B 17/00* (2013.01); *A61L 9/12* (2013.01); *B60H 3/00* (2013.01); *B60H 3/0028* (2013.01); *A61L 2209/133* (2013.01); *A61L 2209/134* (2013.01)

(58) Field of Classification Search
CPC ..... B05B 17/00; A61L 9/12; A61L 2209/133; A61L 2209/134; B60H 3/00
USPC .............. 239/302, 583, 34–60; 137/588, 587, 137/613; 222/321.7–321.9, 383.1
See application file for complete search history.

(56) References Cited

U.S. PATENT DOCUMENTS 5,060,864 A * 10/1991 Nishi .................... B05B 7/2416 180/286
6,364,178 B1 * 4/2002 Paczonay ............... B67D 3/046 222/484
6,592,813 B1 * 7/2003 Fox ........................... A61L 9/01 239/3

(Continued)

FOREIGN PATENT DOCUMENTS

EP        0361437 A2    4/1990
WO        0001421 A1    1/2000
WO    2011101384 A1    8/2011

OTHER PUBLICATIONS

The International Bureau of WIPO, International Preliminary Report on Patentability for the corresponding PCT/EP2012/051698 mailed Aug. 15, 2013.

*Primary Examiner* — Len Tran
*Assistant Examiner* — Joel Zhou
(74) *Attorney, Agent, or Firm* — Brooks Kushman P.C.

(57) ABSTRACT

A functional head for a fragrance container includes a housing wall section and a spring-loaded valve plate. The housing wall section has an inlet opening for admitting air into an inlet channel, an outlet opening for discharging a mixture of fragrance and air from an outlet channel, and a recess. The valve plate is biased to close the openings and is displaceable by a plunger inserted into the recess to thereby open the openings.

19 Claims, 4 Drawing Sheets

(56) References Cited

U.S. PATENT DOCUMENTS 8,113,239 B2 * 2/2012 Richards ............... B67D 3/044 137/587

8,702,018 B1 * 4/2014 Rivera ............... E03C 1/0408 137/888

2005/0185940 A1 * 8/2005 Joshi ............... A01M 1/2033 392/390

* cited by examiner

FUNCTIONAL HEAD FOR A FRAGRANCE CONTAINER

CROSS-REFERENCE TO RELATED APPLICATIONS

This application is a continuation-in-part of International Application No. PCT/EP2012/051698, published in German, with an International filing date of Feb. 1, 2012, which claims priority to DE 10 2011 010 277.9, filed Feb. 4, 2011; the disclosures of which are incorporated in their entirety by reference herein.

TECHNICAL FIELD

The present invention relates to a functional head for a fragrance container, the functional head including an inlet opening for admitting air into an inlet channel, an outlet opening for discharging a mixture of fragrance and air from an outlet channel, and a spring-loaded valve plate which opens the channels when the functional head is attached to a fragrance generator and which closes the channels when the functional head is separated from the fragrance generator.

BACKGROUND

DE 10 2010 008 436 (corresponds to WO 2011/101384) describes this type of functional head for a fragrance container. The functional head includes an inlet opening for admitting air into an inlet channel, an outlet opening for discharging a mixture of fragrance and air from an outlet channel, and a spring-loaded valve plate. The fragrance container is a flacon. The functional head is in the form of a valve cap having the spring-loaded valve plate on its top side. The functional head (i.e., the valve cap) can be screwed on to and unscrewed from the neck of the flacon. The fragrance container with the functional head screwed on is attachable to a fragrance generator to enable delivery of fragrance.

During the attachment process of the fragrance container with the functional head to the fragrance generator, the valve plate pushes against the spring and thereby moves away from (i.e., opens) the inlet and outlet openings. As a result of the valve plate being moved away from the inlet and outlet openings, the inlet and outlet channels are enabled and connected to the fragrance generator. In turn, the fragrance generator introduces an air stream into the inlet channel and discharges the fragrance and air mixture from the outlet channel such as into a vehicle interior.

When the fragrance container with the functional head is separated from the fragrance generator, the spring pushes the valve plate towards the inlet and outlet openings. The valve thereby automatically moves toward and against (i.e., closes) the inlet and outlet openings. As a result, the inlet and outlet channels respectively associated with the inlet and outlet openings are disabled and disconnected from the exterior of the functional head. However, the inlet and outlet channels may be readily reopened upon pressure being applied to the valve plate. As such, there is a risk of liquid fragrance from the fragrance container escaping via the functional head upon an inadvertent pressure being applied to the valve plate.

DE 10 2010 008 436 addresses this risk with a protective cap for the functional head. The protective cap is placed on the functional head to prevent an inadvertent pressure from being applied to the valve plate when the fragrance container with the functional head is removed from the fragrance generator. However, the protective cap is sometimes not at hand upon removal of the fragrance container with the functional head from the fragrance generator. As a result, the user is forced to leave the fragrance container without the protective cap on the functional head. As such, when the fragrance container cannot be placed in a stable upright position, which may occur in particular when used in a vehicle, there is a risk that the valve plate may come into contact with other objects and thus experience an application of pressure causing the valve plate to enable the inlet and outlet channels. Consequently, fragrance in concentrated liquid form may escape from the fragrance container via the channels and the openings of the functional head. Since by their nature fragrances are substances having a very intense odor, unpleasant contamination of the vehicle interior may result which is removable, if at all, only with significant effort.

SUMMARY

An object of the present invention includes a functional head for a fragrance container in which the functional head prevents unintentional release of liquid fragrance from the fragrance container and resulting fragrance contamination with a relatively high level of certainty.

In carrying out at least one of the above and other objects, the present invention provides a functional head for a fragrance container. The functional head includes a housing wall section and a spring-loaded valve plate. The housing wall section has an inlet opening for admitting air into an inlet channel, an outlet opening for discharging a mixture of fragrance and air from an outlet channel, and a recess. The valve plate is biased to close the openings and is displaceable by a plunger inserted into the recess to thereby open the openings.

Further, in carrying out at least one of the above and other objects, the present invention provides a fragrance system. The fragrance system includes a fragrance container and a functional head. The functional head is attached to the fragrance container. The functional head has an inlet opening for admitting air into an inlet channel in communication with the fragrance container, an outlet opening for discharging a mixture of fragrance and air from an outlet channel in communication with the fragrance container, and a spring-loaded valve plate biased to close the openings and being displaceable by a plunger upon the plunger being inserted into the functional head to thereby open the openings.

A functional head for a fragrance container in accordance with embodiments of the present invention includes an inlet opening in communication with an inlet channel, an outlet opening in communication with an outlet channel, and a spring-loaded valve plate. The inlet opening is for admitting air into the inlet channel. The outlet opening is for discharging a mixture of fragrance and air from the outlet channel. The inlet and outlet channels are in communication with the fragrance container when the functional head is attached to the fragrance container.

The valve plate opens the inlet and outlet openings when the functional head is attached to a fragrance generator such that the inlet and outlet channels via the inlet and outlet openings are in communication with the fragrance generator. The valve plate closes the inlet and outlet openings when the functional head is separated from the fragrance generator such that the inlet and outlet channels are not in communication with the exterior of the functional head including the fragrance generator.

The inlet and outlet openings are arranged in a housing wall section of the functional head. The valve plate is arranged in the interior of the functional head and is spring-loaded behind the housing wall section such that the valve plate is biased to close the inlet and outlet openings in the absence of a counter-force against the valve plate. The housing wall section has a recess opening into which a ram, a plunger, or the like can be pushed into in order to provide a counter-force against the valve plate. The valve plate moves counter to the force of the spring upon being pushed by the ram to thereby move away from and open the inlet and outlet openings, whereby the inlet and outlet channels via the inlet and outlet openings are in communication with the exterior of the functional head.

In an embodiment, the ram is part of a fragrance generator. The ram is pushed into the recess opening of the functional head when the functional head is attached to the fragrance generator. The pushed in ram pushes the valve plate against the spring force to thereby cause the valve plate to move away from the inlet and outlet openings, whereby the inlet and outlet channels via the inlet and outlet openings are in communication with the fragrance generator.

In an embodiment, the functional head includes one or more of the following features. The inlet and outlet openings of the functional head are situated in a housing wall section of the functional head. The valve plate of the functional head is situated inside the functional head behind the housing wall section under spring-loading. The spring-loading of the valve plate causes the valve plate to be biased against the housing wall section and thereby close the inlet and outlet openings in the absence of a counter-force against the valve plate. The housing wall section of the functional head has a recess opening (i.e., a plunger opening). A ram or plunger such as of a fragrance generator may be pushed into the plunger opening to engage the valve plate. The plunger may be pushed further through the plunger opening to provide a counter-force to the valve plate against the force of the spring. The valve plate thereby displaces away from housing wall section and opens the inlet and outlet openings.

In an embodiment, the functional head is attachable to and removable from a fragrance container. The functional head is further attachable to a fragrance generator. The functional head attaches to the fragrance generator by connecting to a coupling device of the fragrance generator. The functional head with the fragrance container attached thereto attaches to the fragrance generator to enable delivery of fragrance from the fragrance container via the functional head and the fragrance generator.

In an embodiment, the functional head is designed such that the valve plate: (i) automatically closes the inlet and outlet openings when the functional head is removed from the coupling device of the fragrance generator; and (ii) cannot be actuated by an unintentional influence from the outside of the functional head. This is achieved in that the valve plate is situated inside the functional head and from there seals off the inlet and outlet openings. The valve plate is thus protected from inadvertent actuation.

The valve plate may be accessed solely via the recess opening in the housing wall section of the functional head. A thin pin-shaped object, referred to herein as a plunger, is necessary in order to move the valve plate through the recess opening. A plunger shaped in this way is fixedly or, by an actuator, movably situated on the coupling device of the fragrance generator. The shape and size of the recess opening in the housing wall section of the functional head may be such that unintentional penetration of a pin-like object may be practically ruled out.

Thus, in an embodiment, the functional head may form a cap which screws onto the fragrance container to thereby attach the functional head to the fragrance container. In an embodiment, the functional head is inseparably connected to the fragrance container, for example, by a flanged collar section. Inadvertent loosening of the connection between the functional head and the fragrance container is also excluded in this way.

In an embodiment, the inlet channel and/or the outlet channel of the functional head each form a respective labyrinth system. As a result, liquid fragrance sloshing around in the fragrance container or in the functional head is not able to reach the inlet opening and/or the outlet opening of the functional head. The labyrinth system may be designed such that, besides the inlet and outlet openings, the valve plate closes an additional valve opening of the inlet channel and/or of the outlet channel located inside the functional head. A reliable seal is achieved in this way.

In an embodiment, the functional head may have a symmetrical structure with respect to the inlet and outlet channels, thus simplifying the construction of the functional head. In an embodiment, detent elements are provided on the functional head for establishing a detent connection with the fragrance generator.

In an embodiment, the functional head is usable as a component of a fragrance system in a motor vehicle.

The above features, and other features and advantages of the present invention are readily apparent from the following detailed description thereof when taken in connection with the accompanying drawings.

DETAILED DESCRIPTION

Figure 1:
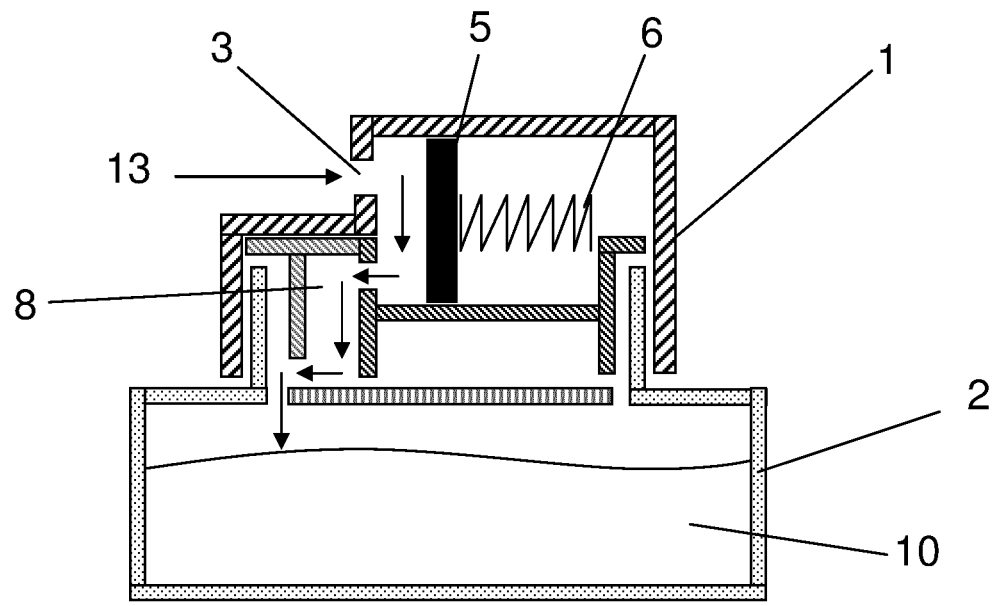
FIG. 1 illustrates a sectional view of a functional head, and a fragrance container attached thereto, in accordance with an embodiment of the present invention along the inlet opening of the functional head.

Detailed embodiments of the present invention are disclosed herein; however, it is to be understood that the disclosed embodiments are merely exemplary of the present invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Referring now to the Figures, a functional head 1 in accordance with an embodiment of the present invention will be described. Functional head 1 is attachable to and removable from a fragrance container 2. Fragrance container 2 is filled with a liquid fragrance 10. Functional head 1 attaches to fragrance container 2 in a liquid-tight manner. Functional head 1 is either screwed to the neck of fragrance container 2 or inseparably connected to fragrance container 2 in some other way. The illustrated arrangement is attachable to an electric device such as a fragrance generator and may be a component of a fragrance system which is used in a motor vehicle, for example.

Functional head 1 includes an inlet opening 3 in communication with an inlet channel 8, an outlet opening 4 in communication with an outlet channel 9, and a spring-loaded valve plate 5. Inlet opening 3 is for admitting air into inlet channel 8. Outlet opening 4 is for discharging a mixture of fragrance and air from outlet channel 9. Inlet and outlet channels 8, 9 are in communication with fragrance container 2 when functional head 1 is attached to fragrance container 2 (shown in FIGS. 1, 2, and 5).

Functional head 1 is further attachable to a fragrance generator (not shown). Functional head 1 attaches to the fragrance generator by connecting to a coupling device of the fragrance generator. Functional head 1 with fragrance container 2 attached thereto attaches to the fragrance generator to enable delivery of fragrance from fragrance container 2 via functional head 1 and the fragrance generator.

Valve plate 5 opens inlet and outlet openings 3, 4 (shown in FIGS. 1 and 2) when functional head 1 is attached to the fragrance generator such that inlet and outlet channels 8, 9 via inlet and outlet openings 3, 4 are in communication with the fragrance generator. Valve plate 5 closes inlet and outlet openings 3, 4 (shown in FIG. 5) when functional head 1 is separated from the fragrance generator such that inlet and outlet channels 8, 9 are not in communication with the exterior of the functional head including the fragrance generator.

Inlet and outlet openings 3, 4 are arranged in a housing wall section 12 of functional head 1. Valve plate 5 is arranged in the interior of functional head 1 and is spring-loaded behind housing wall section 12 such that valve plate 5 is biased to close inlet and outlet openings 3, 4 in the absence of a counter-force against valve plate 5. Housing wall section 12 has a recess opening 7 (e.g., a plunger opening) into which a ram (e.g., a plunger 18) (shown in FIG. 3A) can be pushed into in order to provide a counter-force against valve plate 5. Valve plate 5 moves counter to the force of spring 6 upon being pushed by the plunger 18 to thereby move away from and open inlet and outlet openings 3, 4, whereby inlet and outlet channels 8, 9 via inlet and outlet openings 3, 4 are in communication with the exterior of functional head (shown in FIGS. 1 and 2).

Figure 2:
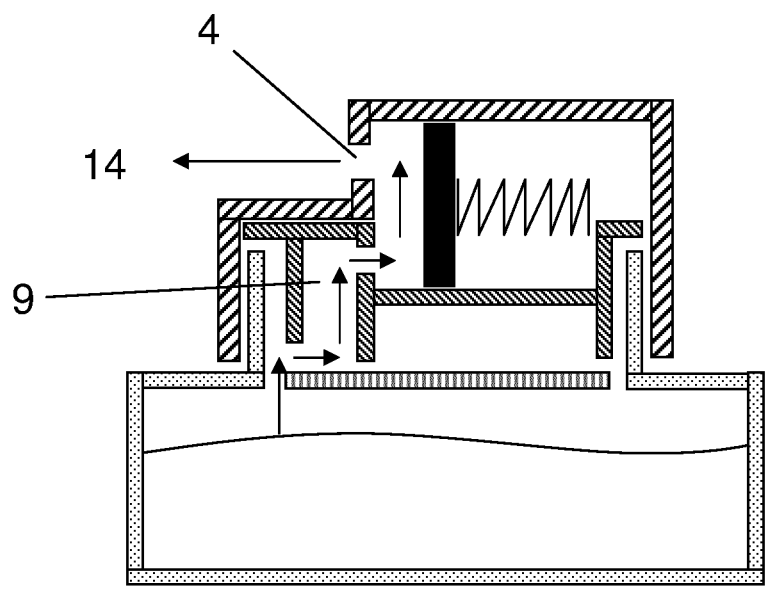
FIG. 2 illustrates a sectional view of the functional head and the fragrance container attached thereto along the outlet opening of the functional head.
Figure 5:
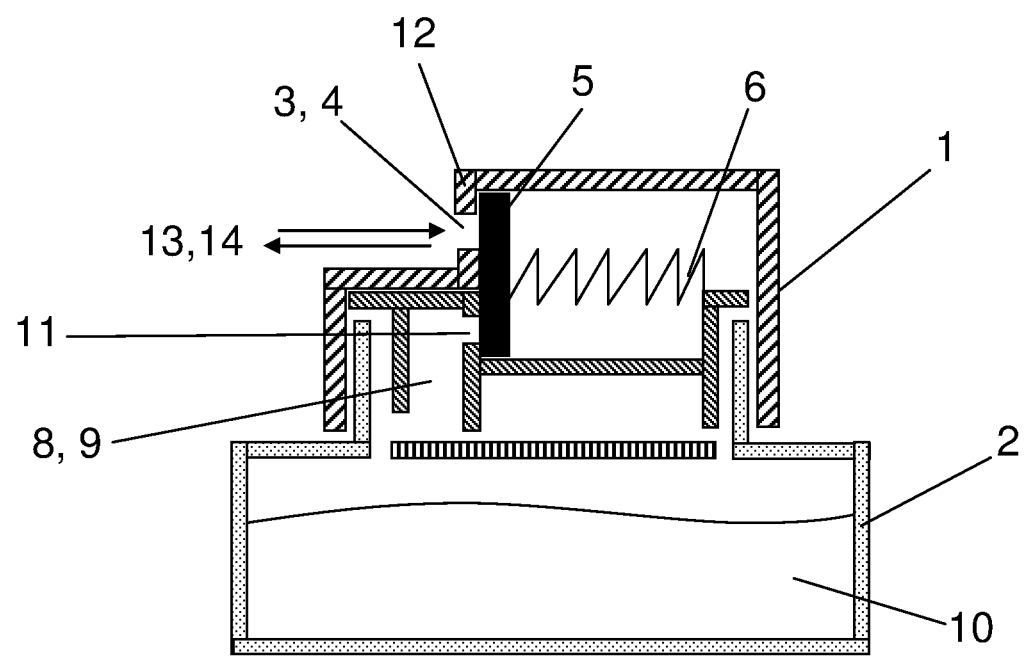
FIG. 5 illustrates a sectional view of the functional head and the fragrance container attached thereto with the valve plate sealing off the inlet and outlet openings.

Functional head 1 further includes an inlet channel opening (shown in FIG. 1, labeled 11 in FIG. 5) and an outlet channel opening (shown in FIG. 2, labeled 11 in FIG. 5). The inlet channel opening is part of inlet channel 8 and results from the labyrinth-like structure of inlet channel 8. The outlet channel opening is part of outlet channel 9 and results from the labyrinth-like structure of outlet channel 9. The inlet channel opening and the outlet channel opening are both arranged in housing wall section 12 of functional head 1. The inlet channel opening corresponds to inlet opening 3 and is arranged in housing wall section 12 below inlet opening 3. The outlet channel opening corresponds to outlet opening 4 and is arranged in housing wall section 12 below outlet opening 4.

FIG. 1 illustrates a sectional view of functional head 1, and fragrance container 2 attached thereto, along inlet opening 3 of functional head 1. The section plane illustrated in FIG. 1 extends through inlet opening 3 of functional head 1. In a fragrance system, air from a fragrance generator attached to functional head 1 is introduced into fragrance container 2 via inlet opening 3 and inlet channel 8 connected thereto. The path of air stream 13 entering functional head 1 from inlet opening 3 through the labyrinth-like inlet channel 8, provided with multiple bends, into fragrance container 2 is indicated by a sequence of directional arrows shown in FIG. 1.

FIG. 2 illustrates a sectional view of functional head 1 and fragrance container 2 attached thereto along outlet opening 4 of functional head 1. The section plane illustrated in FIG. 2 extends through outlet opening 4 of functional head 1. The air enriched with molecules of fragrance 10 passes through outlet channel 9 and outlet opening 4 of functional head 1 to the fragrance generator. The fragrance generator discharges the air/fragrance mixture 14 into the interior of the vehicle. FIG. 2 illustrates the path of the exiting air stream 14, once again by a series of directional arrows. As shown by a comparison of FIGS. 1 and 2, the inlet and outlet regions of functional head 1 may have a symmetrical or even identical design, so that the level of complexity for the construction of functional head 1 may be kept relatively low.

Figure 3:
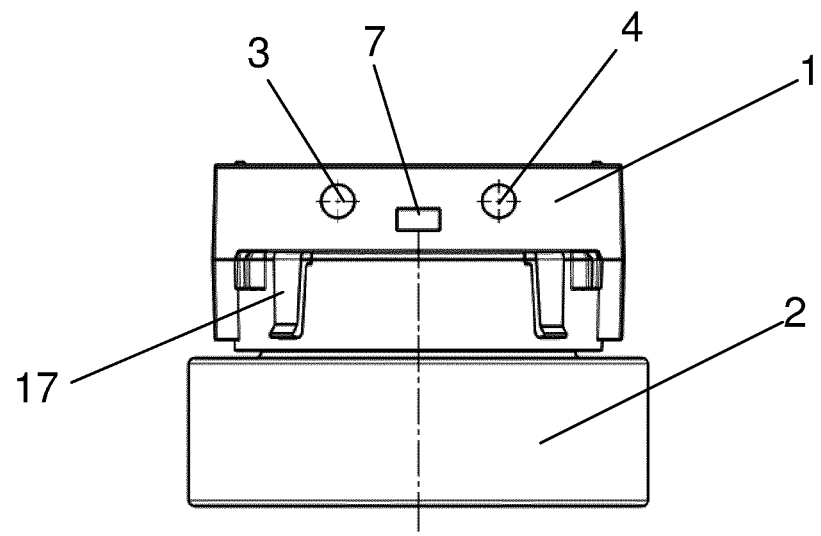
FIG. 3 illustrates a top external view of the functional head and the fragrance container attached thereto.
Figure 3A:
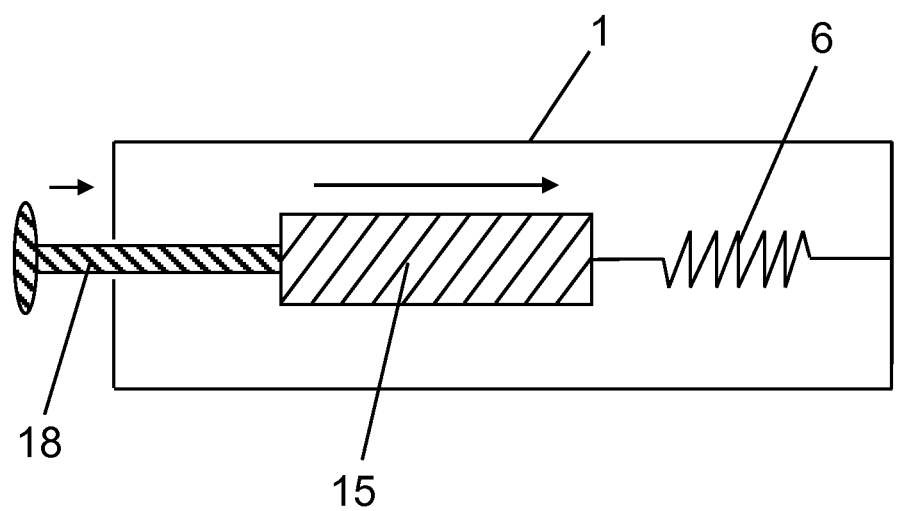
FIG. 3A illustrates a cross-sectional view of the functional head along the segmented line shown in FIG. 3 running through a recess of the functional head with a plunger inserted into the functional head through the recess.

FIG. 3 illustrates a top external view of functional head 1 and fragrance container 2 attached thereto. Inlet opening 3 and outlet opening 4 of housing wall section 12 of functional head 1 are in communication with the exterior of functional head 1. Plunger opening 7 of housing wall section 12 of functional head 1 is between inlet and outlet openings 3, 4 and is also in communication with the exterior of functional head 1. Plunger opening 7 provides access to valve plate 5 (in particular, plunger opening 7 provides access to an actuating region 15 of valve plate 5).

Figure 4:
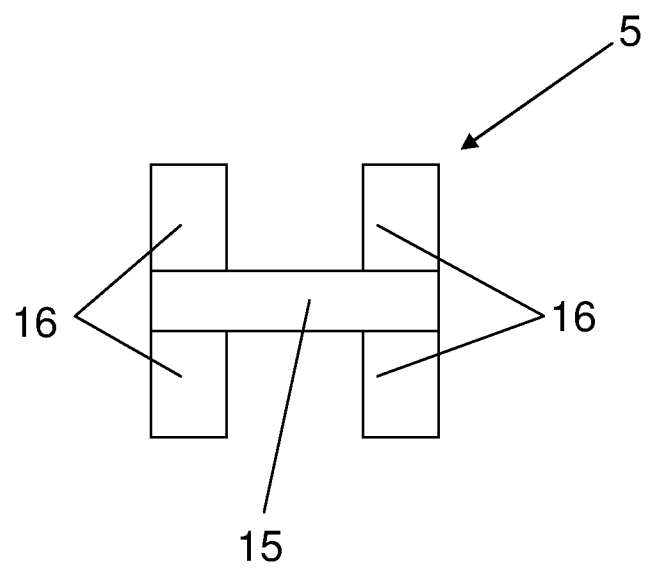
FIG. 4 illustrates the valve plate of the functional head as an individual part.

FIG. 4 illustrates valve plate 5 as an individual part. Valve plate 5 includes an actuating region 15 and a plurality of sealing areas 16. In this embodiment, valve plate 5 includes a total of four sealing areas 16 at sections protruding perpendicularly from actuating region 15. Sealing areas 16 respectively correspond to inlet opening 3, outlet opening 4, the inlet channel opening, and the outlet channel opening. Sealing areas 16 are suitably designed for closing and opening inlet opening 3, outlet opening 4, the inlet channel opening, and the outlet channel opening in a liquid tight manner.

FIG. 5 illustrates a sectional view of functional head 1 and fragrance container 2 attached thereto with valve plate 5 sealing off inlet and outlet openings 3, 4. When a plunger is not engaged with plunger opening 7, spring 6 presses valve plate 5 against the inner side of housing wall section 12 as shown in FIG. 5. As a result, valve plate 5 closes inlet and outlet openings 3, 4 as well as the inlet and outlet channel openings. Due to the symmetrical structure of the inlet and outlet regions of functional head 1, these valve functions, which are actually implemented spatially adjacent to one another, are depicted here by a single illustration. Valve plate 5 thus forms a double valve in each case inside functional head 1, on the side of inlet channel 8 and on the side of outlet channel 9, which on the one hand seals off inlet and outlet openings 3, 4, respectively, and thus protects functional head 1 from the penetration of contaminants, and on the other hand seals off fragrance container 2 to prevent liquid fragrance 10 from escaping.

In an embodiment, the plunger 18 is a component of a coupling device provided on the fragrance generator. To place the fragrance system in the operational state, functional head 1 is connected to the coupling device of the fragrance generator and attached thereto by detent elements 17 integrally molded onto functional head 1. At the same time, connecting elements of the fragrance generator are respectively connected to inlet opening 3 and to outlet opening 4. When functional head 1 is attached to the fragrance generator, the plunger 18 situated on the fragrance generator engages with plunger opening 7 and is pushed through plunger opening 7. The pushed in plunger 18 pushes valve plate 5 against the spring force to thereby cause valve plate 5 to move away from inlet and outlet openings 3, 4, whereby inlet and outlet channels 8, 9 via inlet and outlet openings 3, 4 become in communication with the fragrance generator. That is, moving valve plate 5 against the force of spring 6 opens inlet and outlet openings 3, 4, respectively, the access points to inlet channels and outlet channels 8, 9, respectively, and the internal inlet and outlet channel openings 11.

REFERENCE SYMBOLS

1 Functional head
2 Fragrance container
3 Inlet opening
4 Outlet opening
5 Valve plate
6 Spring
7 Recess opening (plunger opening)
8 Inlet channel
9 Outlet channel
10 Fragrance
11 Valve opening(s)
12 Housing wall section
13 Air stream
14 Fragrance and air stream
15 Actuating region
16 Sealing areas
17 Detent elements
18 Plunger While exemplary embodiments are described above, it is not intended that these embodiments describe all possible forms of the present invention. Rather, the words used in the specification are words of description rather than limitation, and it is understood that various changes may be made without departing from the spirit and scope of the invention. Additionally, the features of various implementing embodiments may be combined to form further embodiments of the present invention.

What is claimed is:

1. A functional head for a fragrance container, the functional head comprising: a housing wall section separating an interior from an exterior, the housing wall section having an inlet opening for admitting air into an inlet channel, an outlet opening for discharging a mixture of fragrance and air from an outlet channel, and a recess, wherein the openings and the recess provide respective access points directly between the interior and the exterior; and a spring-loaded valve plate situated behind the housing wall section within the interior and biased to close the openings, the valve plate being displaceable by a plunger inserted from the exterior into the interior through the recess to thereby open the openings and the housing wall section otherwise preventing displacement of the valve plate from the exterior displacement of the valve plate from the exterior, wherein the biasing of the valve plate causes the valve plate to close the openings upon the plunger inserted into the interior being removed from the interior.

2. The functional head of claim 1 wherein:
the channels are in communication with the fragrance container when the functional head is attached to the fragrance container.

3. The functional head of claim 1 wherein:
the channels via the openings are in communication with the exterior of the functional head when the valve plate opens the openings.

4. The functional head of claim 1 wherein:
the channels are not in communication with the exterior of the functional head when the valve plate closes the openings.

5. The functional head of claim 1 wherein:
the inlet channel and the outlet channel each include multiple bends.

6. The functional head of claim 1 wherein:
the functional head has a symmetrical structure with respect to the inlet channel and the outlet channel.

7. The functional head of claim 1 wherein:
the housing wall section further has an inlet channel opening and an outlet channel opening, the inlet channel opening being in communication between the inlet opening and the inlet channel and the outlet channel opening being in communication between the outlet opening and the outlet channel opening;
wherein the valve plate is further configured to close the inlet channel opening and the outlet channel opening when biased and to open the inlet channel opening and the outlet channel opening when displaced by a plunger inserted into the recess.

8. The functional head of claim 1 further comprising:
detent elements for establishing a connection of the functional head with a fragrance generator.

9. The functional head of claim 1 wherein:
the functional head is for use in a fragrance system in a vehicle.

10. The functional head of claim 1 wherein:
the functional head forms a cap which can be screwed onto the fragrance container.

11. The functional head of claim 1 wherein:
the functional head is inseparably attached to the fragrance container.

12. A fragrance system comprising: a fragrance container; and a functional head attached to the fragrance container, the functional head separating an interior from an exterior and having an inlet opening for admitting air into an inlet channel in communication with the fragrance container, an outlet opening for discharging a mixture of fragrance and air from an outlet channel in communication with the fragrance container, and a recess, wherein the openings and the recess provide respective access points directly between the interior and the exterior, the functional head further having a spring-loaded valve plate situated within the interior and biased to close the openings, the valve plate being displaceable by a plunger upon the plunger being inserted from the exterior into the interior through the recess to thereby open the openings and the functional head otherwise preventing displacement of the valve plate from the exterior, wherein the biasing of the valve plate causes the valve plate to close the openings upon the plunger inserted into the functional head being removed from the functional head.

13. The fragrance system of claim 12 wherein:
the functional head further includes a recess configured to receive and enable a plunger to be inserted into the functional head to thereby displace the valve plate and open the openings.

14. The fragrance system of claim 12 wherein:
the functional head further having an inlet channel opening and an outlet channel opening, the inlet channel opening being in communication between the inlet opening and the inlet channel and the outlet channel opening being in communication between the outlet opening and the outlet channel opening;
wherein the biasing of the valve plate causes the valve plate to close the inlet channel opening and the outlet channel opening in addition to closing the inlet opening and the outlet opening;
wherein displacement of the valve plate by a plunger upon the plunger being inserted into the functional head causes the valve plate to open the inlet channel opening and the outlet channel opening in addition to opening the inlet opening and the outlet opening.

15. The fragrance system of claim 12 wherein:
the valve plate opens the openings when the functional head is attached to a frequency generator having a plunger upon the plunger being inserted into the functional head during the attachment of the functional head to the frequency generator.

16. The fragrance system of claim 15 wherein:
the valve plate closes the openings when the functional head is separated from the frequency generator having the plunger upon the plunger being removed from the functional head during the separation of the functional head from the frequency generator.

17. The fragrance system of claim 15 wherein:
the functional head includes detent elements for attaching the functional head to the fragrance generator.

18. The fragrance system of claim 12 wherein:
the inlet channel and the and outlet channel each include multiple bends.

19. The fragrance system of claim 12 wherein:
the functional head has a symmetrical structure with respect to the inlet channel and the outlet channel.

* * * * *